United States Patent [19]
Goding et al.

[11] Patent Number: 5,932,441
[45] Date of Patent: Aug. 3, 1999

[54] VECTORS FOR DIFFERENTIAL EXPRESSION

[75] Inventors: Colin Ronald Goding, Purley; Michael White, Warrington; Bahriye Ugur Yavuzer, Cambridge; Douglas Hurd, Oxford, all of United Kingdom

[73] Assignee: Amersham International PLC, Buckinghamshire, United Kingdom

[21] Appl. No.: 08/930,274

[22] PCT Filed: Mar. 29, 1996

[86] PCT No.: PCT/GB96/00765

§ 371 Date: Jan. 20, 1998

§ 102(e) Date: Jan. 20, 1998

[87] PCT Pub. No.: WO96/30507

PCT Pub. Date: Oct. 3, 1996

[30] Foreign Application Priority Data

Mar. 31, 1995 [EP] European Pat. Off. .............. 95302196

[51] Int. Cl.⁶ ...................................................... C12P 21/02

[52] U.S. Cl. ......................................... 435/69.1; 435/320.1

[58] Field of Search ................................. 435/69.1, 320.1

[56] References Cited

PUBLICATIONS

S. Fields et al. "A novel genetic system to detect protein–protein interactions", Letters to Nature, vol. 340, pp. 245–246, Jul. 20, 1989.

S. Green et al., "A versatile in vivo and in vitvo eucaryotic expression vector for protein engineering", Nucleic Acids Research, vol. 16, No. 1, pp. 268–269, Jan. 11, 1988.

*Primary Examiner*—James Ketter
*Attorney, Agent, or Firm*—Wenderoth, Lind & Ponack,L.L.P.

[57] ABSTRACT

DNA constructs and vectors are provided for differential expression of proteins in different expression systems, to enable expression of a protein of interest alone or as part of a fusion protein without the need to transfer the coding sequence for the protein of interest from one vector to another.

14 Claims, 6 Drawing Sheets

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 28 base pairs
        (B) TYPE: nucleic acid
        (C) STRANDEDNESS: single
        (D) TOPOLOGY: linear     (ii) MOLECULE TYPE: other nucleic acid
        (A) DESCRIPTION:   /desc = "synthetic primer"

(xi) SEQUENCE DESCRIPTION: SEQ ID NO: 1:

AGACGAGCTC GAAGTACGGA TTAGAAGC                                           28

(2) INFORMATION FOR SEQ ID NO: 2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic primer"

(xi) SEQUENCE DESCRIPTION: SEQ ID NO: 2:

AGACTCTAGA TGTTGATACT TTTATTACAT TTG                                          33

(2) INFORMATION FOR SEQ ID NO: 3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic primer"

(xi) SEQUENCE DESCRIPTION: SEQ ID NO: 3:

AGACTCTAGA ATGTCGACGG CCCCCCCGAC CGAT                                         34

(2) INFORMATION FOR SEQ ID NO: 4:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic primer"

(xi) SEQUENCE DESCRIPTION: SEQ ID NO: 4:

AGAGGATCCA GATCTTCATA GTTAGTCACC CACCGTACTC GTCAATTCC                         49

(2) INFORMATION FOR SEQ ID NO: 5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic primer"

(xi) SEQUENCE DESCRIPTION: SEQ ID NO: 5:

AGACCTCGAG CATGCATCTA GAGGGCCGCA TCATGTAATT AG                                42

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic primer"

(xi) SEQUENCE DESCRIPTION: SEQ ID NO: 6:

AGACGGTACC GGCCGCAAAT TAAAGCCTTC                                              30

(2) INFORMATION FOR SEQ ID NO: 7:

```
    (i) SEQUENCE CHARACTERISTICS:
        (A) LENGTH: 13 base pairs
        (B) TYPE: nucleic acid
        (C) STRANDEDNESS: double
        (D) TOPOLOGY: linear (ii) MOLECULE TYPE: other nucleic acid
        (A) DESCRIPTION:   /desc = "restriction site"

(xi) SEQUENCE DESCRIPTION: SEQ ID NO: 7:

CCAACTGCAT GGA                                                           13

(2) INFORMATION FOR SEQ ID NO: 8:

(i) SEQUENCE CHARACTERISTICS:
        (A) LENGTH: 13 base pairs
        (B) TYPE: nucleic acid
        (C) STRANDEDNESS: double
        (D) TOPOLOGY: linear (ii) MOLECULE TYPE: other nucleic acid
        (A) DESCRIPTION:   /desc = "mutated restriction site"

(xi) SEQUENCE DESCRIPTION: SEQ ID NO: 8:

ACAACTGCAT GGA                                                           13

(2) INFORMATION FOR SEQ ID NO: 9:

(i) SEQUENCE CHARACTERISTICS:
        (A) LENGTH: 133 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 9:

CAGATCTATT AATACGACTC ACTATAGGGA GACCACAAGG TTTCCATCTA GAGTTCTTTA         60

CAAGAGAAGG AGTTCCCTGC AGGCAGCTGT GTGGATCCAT GGTACCAGCG GCCGCTAGCT        120

AGCTGACTCG AGG                                                          133

(2) INFORMATION FOR SEQ ID NO: 10:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 10:

CCTCGAGTCA GCTAGCTAGC GGCCGCTGGT ACCATGGATC CACAGCTGCC TGCAGGGAAC         60

TCCTTCTCTT GTAAAGAACT CTAGATGGAA ACCTTGTGGT CTCCCTATAG TGAGTCGTAT        120

TAATAGATCT GAGCT                                                        135

(2) INFORMATION FOR SEQ ID NO: 11:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: other nucleic acid
```

(A) DESCRIPTION:   /desc = "synthetic DNA"

(xi) SEQUENCE DESCRIPTION: SEQ ID NO: 11:

GGGTATGCAC CACCACCACC ACCACGCTAT GGCTAGCATG ACTGGCGGTC AGCAAATGGG     60

TAGAATTCAA ACCAGTGTGC TGGAGTTAAC AAAGCTTAAG TCGACCATCA CACTG        115

(2) INFORMATION FOR SEQ ID NO: 12:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 12:

GATCCAGTGT GATGGTCGAC TTAAGCTTTG TTAACTCCAG CACACTGGTT TGAATTCTAC     60

CCATTTGCTG ACCGCCAGTC ATGCTAGCCA TAGCGTGGTG GTGGTGGTGG TGCATACCCT    120

GCA                                                                  123

(2) INFORMATION FOR SEQ ID NO: 13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 13:

AATTGAGATC TGATATCGGT CCCTCGAG                                        28

(2) INFORMATION FOR SEQ ID NO: 14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 14:

GATCCTCGAG GGACCGATAT CAGATCTC                                        28

(2) INFORMATION FOR SEQ ID NO: 15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 15:

GGATTTCGAA ATGCACCACC ACCACCACCA CGCTATGG                             38

(2) INFORMATION FOR SEQ ID NO: 16:

(i) SEQUENCE CHARACTERISTICS:

(A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 16:

CTAGCCATAG CGTGGTGGTG GTGGTGGTGC ATTTCGAAAT CCTGCA                46

(2) INFORMATION FOR SEQ ID NO: 17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic primer"

(xi) SEQUENCE DESCRIPTION: SEQ ID NO: 17:

GGAAGCTTAT GAAAGCGTTA ACGGCCAGGC AACAAGAGG                       39

(2) INFORMATION FOR SEQ ID NO: 18:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic primer"

(xi) SEQUENCE DESCRIPTION: SEQ ID NO: 18:

GAAGCTTCTC GAGGAGATAG ATCTCAGCCA GTCGCCGTTG CG                   42

(2) INFORMATION FOR SEQ ID NO: 19:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 19:

GGGTATGAAA GAAACCGCTG CTGCTAAATT CGAAAGACAG CACATGGACA GCGATATCAG    60

(2) INFORMATION FOR SEQ ID NO: 20:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 20:

AATTCTGATA TCGCTGTCCA TGTGCTGTCT TTCGAATTTA GCAGCAGCGG TTTCTTTCAT    60

ACCCTGCA                                                            68

(2) INFORMATION FOR SEQ ID NO: 21:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic primer"

(xi) SEQUENCE DESCRIPTION: SEQ ID NO: 21:

CGGATCCGCA GAATTCTTAA CAAGCGCAGA GGTAAACC                                      38

(2) INFORMATION FOR SEQ ID NO: 22:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic primer"

(xi) SEQUENCE DESCRIPTION: SEQ ID NO: 22:

GGGTCGACCT CACGTGCTCT CGTTC                                                    25

(2) INFORMATION FOR SEQ ID NO: 23:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic primer"

(xi) SEQUENCE DESCRIPTION: SEQ ID NO: 23:

GCGCAGAATT CGGATCCAAA TGGAAAGCAC ATCAGGAGAA                                    40

(2) INFORMATION FOR SEQ ID NO: 24:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic primer"

(xi) SEQUENCE DESCRIPTION: SEQ ID NO: 24:

AGATCTAATC TGCCTTTGAT CGCTTGTTA                                                29

(2) INFORMATION FOR SEQ ID NO: 25:

(i) SEQUENCE CHARACTERISTICS:
            (A) LENGTH: 201 base pairs
            (B) TYPE: nucleic acid
            (C) STRANDEDNESS: double
            (D) TOPOLOGY: circular (ii) MOLECULE TYPE: other nucleic acid
            (A) DESCRIPTION:   /desc = "part of recombinant DNA vector"

(xi) SEQUENCE DESCRIPTION: SEQ ID NO: 25:

```
AGATCCAGAT CTTTAATACG ACTCACTATA GGGAGACCAG AAGAAGGAGA TCCCTCTAGC      60

ATGGGAAAGC CGATCCCAAA CCCTTTGCTG GGATTGGACT CCGAGCTCGG ATCTGGATCC     120

ACTAGTAACG GCCGCCAGTG TGCTGGAATT CTGCAGATAT CCATCACACT GGCGGCCGCT     180

CGAGCATGCA TCTAGAGGGC C                                              201
```

VECTORS FOR DIFFERENTIAL EXPRESSION

This invention relates to nucleic acid constructs capable of being differentially expressed, and to vectors comprising such constructs. The invention further relates to a method for differential expression of a protein.

Various expression systems are available for synthesising proteins. For expression in eukaryotic cells such as mammalian cells or yeast, a protein coding DNA sequence may be placed downstream of a promoter and introduced into the appropriate host cell. RNA transcribed under control of the promoter will then be translated by the host cell translation machinery including ribosomes.

Proteins may also be expressed in vitro. In this case, the coding sequence is most usually placed downstream from a bacteriophage promoter which directs the synthesis of RNA in the presence of a suitable polymerase. The RNA is then used to programme a cell-free extract, derived eg. from rabbit reticulocytes, which contains ribosomes and other components of the translation machinery.

A further alternative is to express proteins in bacteria. This can be achieved by placing the coding sequence downstream of a promoter DNA sequence which acts as a recognition sequence for either a bacterial or bacteriophage RNA polymerase. A commonly used system involves introducing a ribosome binding site 5' to the ATG initiation codon for the protein sequence, where the ribosome begins translation of the RNA. The DNA sequence thus produced is introduced into bacteria which constitutively express a compatible RNA polymerase. The bacteriophage promoter drives the production of RNA which will then be translated by ribosomes recognising the ribosome binding site and the ATG initiation codon.

As a result of the differences between mammalian, yeast, bacterial and bacteriophage promoters, in order to achieve transcription and subsequent translation of a particular protein coding sequence in the different systems, it is necessary to transfer the coding sequence from one expression vector to another. The transfer is a time-consuming step.

In some cases it is also desirable to express different but related forms of the same protein in the different systems. For example, expression of a protein in yeast may be "tagged" with an epitope for identification with an antibody, or with part of a heterologous protein, such as a transcriptional activation domain.

In the two-hybrid assay technique of Fields and Song described in U.S. Pat. No. 5,283,173, two chimeric genes which encode fusion proteins are used to test the interaction between a known protein and a protein of interest. The first chimeric gene codes for a known protein, fused to a protein domain which binds to any specific DNA sequence such as the DNA binding domain of a transcriptional activator. The second chimeric gene codes for the protein of interest fused to a transcriptional activation domain. Alternatively, the chimeric genes may be reversed, with the protein of interest fused to the DNA-binding domain and the known protein fused to the transcriptional activation domain. Additionally, the protein of interest may not be known and could be derived for example from a cDNA library. In a suitable host cell, if the protein of interest and the known protein do interact, they bring into proximity the DNA-binding and transcriptional activation domains. This proximity is sufficient to cause transcription of a marker gene placed under the control of a promoter containing a binding site for the DNA-binding domain. Once an interaction has been demonstrated, it is often desirable to further investigate the test protein eg. by expressing it in isolated form. The interactions detected ex vivo (that is, in the cell expressing the hybrids) or in vivo eg. yeast or plants or animals require confirmation in vitro and the test proteins may need to be over-expressed in bacteria for the production of antibodies. Transfer to suitable vectors is therefore required.

The present invention aims to avoid the need for transfer between vectors, for example in the situations described above.

The invention therefore provides in one aspect a DNA construct for investigating a protein, which DNA construct comprises:
(a) a first promoter
(b) a chimeric gene comprising a DNA sequence that encodes a fusion protein, said DNA sequence under transcriptional control of the first promoter, such that in a suitable host cell the fusion protein is expressed, the fusion protein comprising:
 (i) a first domain for detecting, quantifying or giving an additional function to the fusion protein;
 (ii) a second domain which is the protein of interest;
characterised in that within the chimeric gene is a second promoter capable of initiating transcription of a portion of the chimeric gene encoding one of the two domains of the fusion protein without the other domain, and the two promoters operate under different conditions.

Thus, by control of transcription under different promoters, differential expression of the chimeric gene may be achieved. The two domains of the fusion protein are encoded by a continuous reading frame which is not interrupted by the second promoter. ATG initiation codons for the fusion and for the second domain are in the same reading frame.

Preferably but not necessarily, the second promoter is capable of initiating transcription of a portion of the chimeric gene encoding the second domain of the fusion protein without the first domain.

The first promoter may be a yeast, plant, insect, mammalian, eukaryotic viral, bacterial, bacteriophage or synthetic promoter sequence which is active in any of the above systems.

The second promoter may also be one of those listed for the first promoter provided that the expression from this second promoter may be differentially controlled.

The choice of promoters will generally depend on which expression system is used for the fusion protein and for the first or second domain whichever is under transcriptional control of the second promoter.

Preferably, the second promoter is one which is capable of initiating transcription in vitro, that is not inside a cell. Bacteriophage promoters such as the T7, T3 and SP6 promoters are particularly suitable since they are directly recognised by relatively simple sequence-specific RNA polymerase enzymes. Alternatively or additionally, the second promoter may be capable of initiating transcription in bacterial cells. For example, a bacterium which expresses a bacteriophage polymerase can be used to express the protein of interest under control of an appropriate bacteriophage promoter.

The first domain of the fusion protein can be any protein which is useful for identifying the fusion protein or performing any sort of specific function in relation to it. The first domain may be for example a reporter protein, an epitope tag, an antibody combining region, a transcriptional activator or DNA-binding domain or a domain allowing binding to a bead or solid surface. The first domain may be capable of performing a number of functions.

Where the first domain is an epitope tag, this could be identified using a specific antibody and labelling system. The first domain may be useful for purification and/or quantification of the fusion protein. For quantification, a first domain comprising a reporter gene such as the luciferase, β-galactosidase or green fluorescent protein (GFP) gene would be suitable.

The first domain may be designed for a functional role in an assay, such as the two-hybrid assay system described above. For one DNA construct, commonly called the activation construct, the first domain could be a transcriptional activation domain and the second domain the first test protein or fragment thereof. In the second counterpart DNA construct, commonly called the bait construct, the first domain could be a DNA binding domain and the second domain a second test protein or fragment, commonly called the bait protein as part of the bait or DNA-binding construct. A functional transcriptional activator protein may be formed from an interaction between the first and second test proteins.

Other additional features of the DNA construct according to the invention which may be desirable include a sequence encoding an epitope, within the chimeric gene. Preferably, the epitope is expressed with the second domain, under control of the second promoter, as well as in the fusion protein under control of the first promoter. Such an epitope will be useful for identifying and/or purifying the second domain when expressed without the remaining part of the fusion protein.

The DNA construct according to the invention is preferably in the form of an expression vector such as a plasmid. Expression vectors which can be easily transferred between systems are especially preferred.

Alternatively, the invention may be in the form of a viral expression vector. For example, a chimeric gene may express a filamentous phage under the control of the first promoter, and have the protein of interest under the control of the second promoter as the second domain. The protein of interest may be for example, either an antibody, peptide or test protein. Differential expression from the two promoters will allow either expression of a complete bacteriophage from the activity of the first promoter, or solely the protein of interest from the second promoter. This system may be applied to a study of protein interactions based on two gene 3 hybrid proteins which have to interact through two test proteins to form a functional infective bacteriophage (Gramatikoff et al., (1994) Nucl. Acids. Res. 22: (25) 5761–5762). In another example the test protein of interest may be expressed in a retroviral vector eg. as a fusion protein with the env gene product. In this case the promoter in the 5' long terminal repeat (LTR) constitutes the first promoter which gives rise to expression of infective retroviral particles and will also give rise to expression of the hybrid env protein at the cell surface. Activity of the second promoter will express the protein of interest in the absence of the membrane targeted env gene product.

In a further aspect, the invention provides a DNA construct as herein defined, wherein the portion of the chimeric gene encoding the second domain of the fusion protein is absent and the chimeric gene contains at least one cloning site for insertion of the absent portion. A DNA sequence encoding a second domain of interest may be inserted into the cloning site. A single design of DNA construct may be used to make a library of constructs encoding different test proteins, derived for example from a cDNA population. A series of constructs according to the invention could also be made based on a single test protein mutagenised in different ways. Mutagenesis of test protein can be useful for example to define regions of the protein, or to alter its binding characteristics. Such libraries or series of constructs may in particular be used to investigate the properties of the test protein by means of the two-hybrid assay.

The DNA construct according to the invention will also normally comprise a transcription terminator of an appropriate type. Where the first promoter is a mammalian promoter, the construct will usually incorporate an intron upstream of the transcription terminator.

The construct will also usually contain suitable initiation and stop codons for translation. In the case of a construct from which the portion of the chimeric gene encoding the second domain is absent, the construct may or may not contain either an initiation codon for the second domain, or a stop codon. When the second domain-encoding sequence to be inserted is, for example, an incomplete cDNA derived from part of mRNA molecule, either or both an initiation codon and a stop codon will need to be present in the DNA construct itself.

In a further aspect, the invention provides a host cell containing a DNA construct or a vector as described herein.

In another aspect the invention provides a method for differential expression of a chimeric protein having at least two domains, comprising:

providing a vector containing a DNA sequence in which a first promoter controls transcription of all of the domains and a second promoter controls transcription of one or more but not all of the domains, the promoters being operational under different conditions;

subjecting the vector to a first set of conditions to effect transcription under the control of the first promoter and expression of a protein comprising all of the domains;

subjecting the vector to a second set of conditions to effect transcription under the control of the second promoter and expression of a protein comprising one or more but not all of the domains.

In the method according to the invention, the promoters and the chimeric protein and its separate domains are preferably as herein described. The first and second set of conditions are preferably different expression systems known in the field or as discussed herein.

A particular advantage of the invention is that it lends itself to automation. Previously, when a protein of interest expressed as part of a fusion protein was to be further investigated in isolation, sub-cloning of the relevant portion of DNA into another vector was necessary. This requires too much judgement for it to be automated. By applying the present invention, it will be possible to automate the differential expression of proteins.

With reference to the attached drawings.

Figure 4:
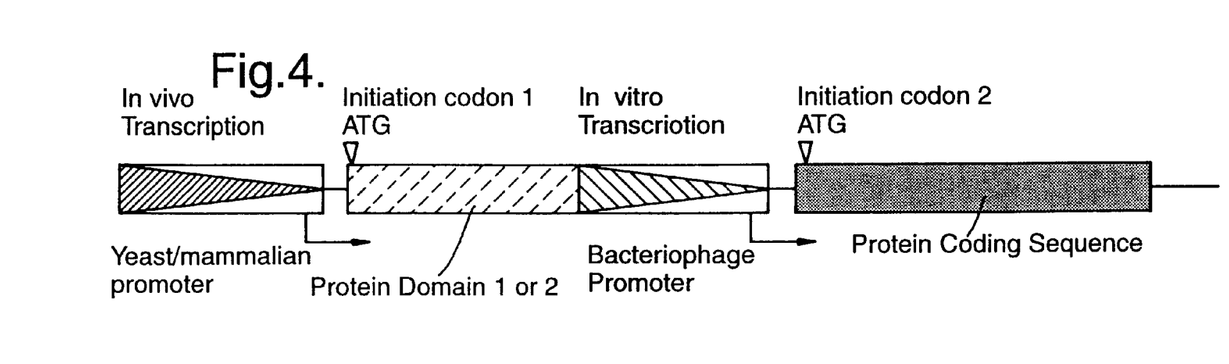
FIG. 4 shows a generalised construct according to one embodiment of the invention.

In the generalised construct according to one embodiment of the invention, as shown in FIG. 4, there is a yeast or mammalian promoter, a first protein sequence with an ATG initiation codon, a bacteriophage promoter and, downstream from the bacteriophage promoter, a second protein coding sequence with an ATG initiation codon. Initiation codons 1 and 2 are in frame.

Figure 5A:
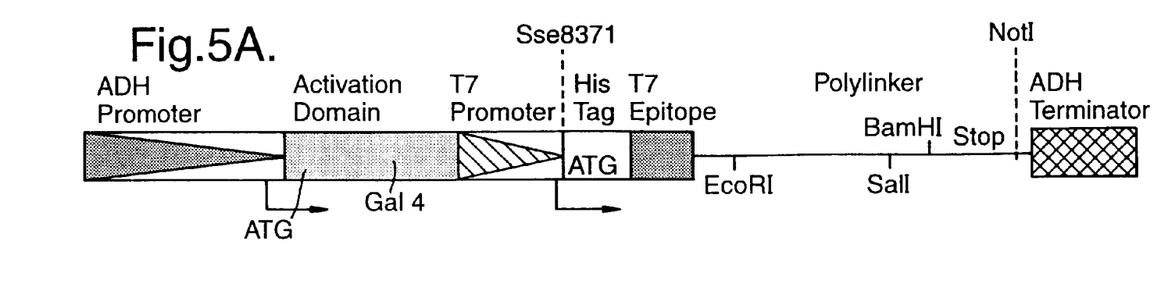
FIGS. 5A and 5B show generalised constructs designed for use in a two-hybrid assay.
Figure 5B:
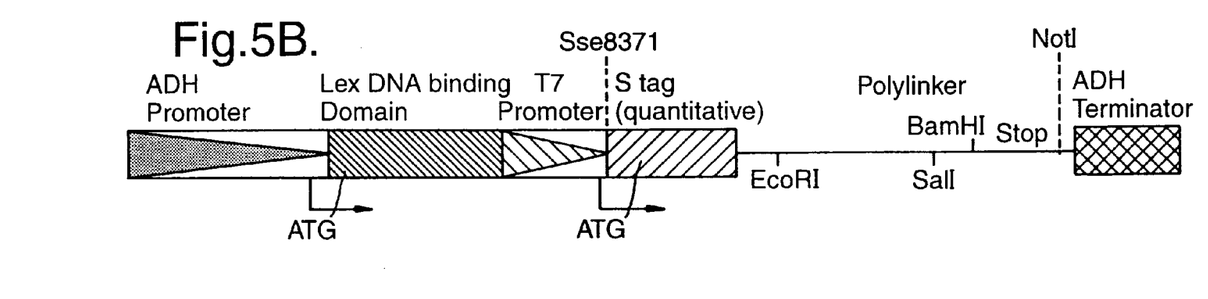

FIGS. 5A and 5B show DNA constructs according to the invention, which are activator and bait constructs respectively without the second domain encoding sequence, and suitable for use as the activator and bait plasmids respectively in the two-hybrid assay. A polylinker DNA sequence between the bacteriophage promoter and a transcriptional terminator eg. yeast ADH1, which contains a number of restriction sites which can be used to insert the test protein DNA. Also present in the polylinker are 3 stop codons in all 3 reading frames for terminating translation. An epitope-encoding sequence is positioned i.n the construct so that it will be expressed with the second domain as well as in the fusion protein. The first promoter used in the both FIG. 5A and FIG. 5B is the ADH1 yeast promoter. The second promoter in both constructs is the T7 bacteriophage promoter. An ATG is positioned downstream of the T7 promoter. This can be provided by the plasmid or the gene of interest. The fusion protein will be expressed in yeast, and for the second domain, the T7 promoter will initiate transcription in vitro or in bacteria such as *E.coli* expressing the relevant polymerase. The first protein domain encoded by the FIG. 5A construct is the GAL4 activation domain. A further optional feature is a nuclear localisation sequence (NLS), for use in the two-hybrid system for example.

FIG. 5B shows a construct which is a bait construct encoding a DNA-binding protein. This construct encodes the Lex DNA-binding portion and the epitope "S tag", and no nuclear localisation sequence, but other than that is similar to the FIG. 5A construct.

The invention will now be further described by the Examples which follow.

EXAMPLES

One important use for the differential expression vectors is likely to be for use in the two-hybrid system. The following examples detail the construction and testing of a series of differential expression vectors in both one and two-hybrid systems. In addition, differential protein expression has been shown in vitro and in *E.coli*.

Examples 1 to 3 describe the construction of a new vector, pWITCH, designed to facilitate the characterisation of proteins encoded by novel cDNAs isolated using either a one- or two-hybrid assay. Expression of directionally cloned cDNAs is directed ex vivo in *S.cerevisiae* from the inducible GAL10 promoter and in vitro or ex vivo in *E.coli* from the T7 promoter while translation of the expressed cDNAs results in proteins which are tagged in vitro with a specific epitope and ex vivo with both the epitope and the VP16 transcription activation domain.

Examples 4–7 describe the construction of two further differential expression vectors pDM22 and pDM26 that can be used together in a two-hybrid assay. In these examples, expression of directionally cloned cDNAs is directed ex vivo in *S.cerevisiae* from an ADH1 promoter and in vitro or ex vivo in a suitable *E.coli* strain from the T7 promoter. Translation of the expressed cDNAs results in proteins which are tagged with specific epitopes both ex vivo and in vitro.

Example 1

Figure 1:
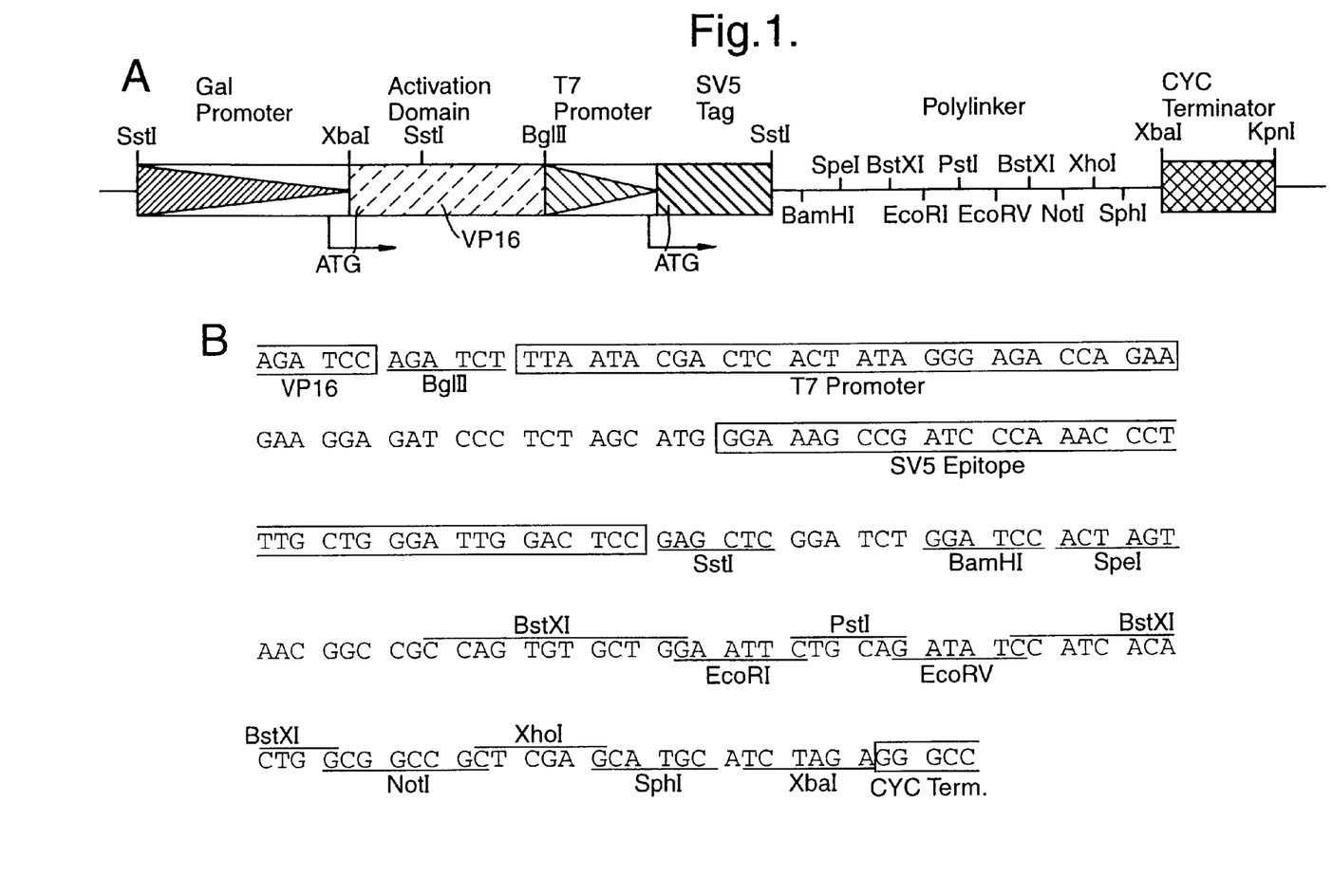
FIGS. 1A and 1B show: A the features of a DNA construct as described in Example 1; B the sequence of the relevant part of the construct (SEQ ID NO. 25)

The design of pWITCH pWITCH combines several features to enable the ex vivo production of cDNA-encoded proteins tagged with an activation domain and an epitope. A map showing relevant features of pWITCH is shown in FIG. 1.

Expression ex vivo is controlled by the galactose-inducible GAL10 promoter enabling protein to be expressed conditionally, and transcription terminated using the CYC terminator sequence.

The activation domain comprises the C-terminal 80 amino acids of the herpes simplex virus VP16, chosen because it is known to function well in yeast (Cousens et al., 1989; Jayaraman et al., 1994) and has not been shown to be subject to any form of regulation. Yeast have been found to grow well while producing VP16 activation domain-tagged proteins from the GAL10 promoter if a low copy number plasmid is used. Two versions of pWITCH were constructed based on the low copy number CEN/ARS plasmids pRS314 or pRS316 (Sikorski and Hieter, 1989) which contain TRP1 and URA3 selectable markers respectively. The TRP1 and URA3 markers were chosen primarily since they are useful selectable markers employed with many yeast strains currently available.

To facilitate expression in vitro, the T7 promoter, which is compatible with currently available commercial in vitro to transcription/translation systems, was placed downstream from the VP16 activation domain.

To enable protein expressed ex vivo or in vitro to be immunoprecipitated or western blotted without the necessity of first raising appropriate antibodies, a 13 amino acid epitope derived from the SV5 virus P and V proteins was provided with an ATG initiation codon and placed in frame with the VP16 activation domain. The SV5 epitope (Hanke et al., 1992) is recognised by a mouse monoclonal antibody and has previously been successfully used for immunoprecipitation, western blotting and immunofluorescence (Hanke et al., 1992 and references therein; Hirst et al., 1994). Other frequently used epitopes or tags are influenza HA, Myc 9E10, (his6), T7, S-tag or glutathione S-transferase.

The most useful commercial cDNA library synthesis kits enable the directional cloning of cDNAs between either BstXI and NotI (Invitrogen) or XhoI and EcoRI restriction sites. To facilitate the insertion of cDNAs synthesised using these commercial kits, BstXI, NotI, XhoI and EcoRI sites were engineered into the pWITCH polylinker located downstream from the SV5 epitope. In the TRP version of pWITCH the BstXI site in the TRP1 gene was mutated in such a way as to leave the TRP1 coding sequence unaltered. Moreover, to make pWITCH a more versatile cloning vector, for use in mapping domains required for protein-:protein interactions for example, additional useful cloning sites (BamHI, PstI, SpeI, SphI) were also introduced into the polylinker.

The method of construction was as follows:

The GAL 10 promoter was isolated by PCR using primers which placed an Sst1 site at the 5' end and an XbaI fragment at the 3' end of the PCR product. The primers used were as follows: 5'-agacgagctcGAAGTACGGATTAGAAGC-3'

(SEQ ID NO. 1) and 5'-agactctagaTGTTGATACTTTTATTACATTTG-3' (SEQ ID NO. 2) and the PCR product was inserted between SstI and XbaI sites of pRS316 to yield pRS316.GAL10p. The sequence encoding the 80 amino acid VP16 activation domain was isolated by PCR using the following primers: 5'-agactctagaATGTCGACGGCCCCCCCGACCGAT-3' (SEQ ID NO. 3) and 5'-agaggatccagatctTCATAGTTAGTCACCCACCGTACTC GTCAATTCC-3' (SEQ ID NO. 4) and was cloned between the XbaI and BamHI sites of pRS316.GAL10p. The CYC terminator was isolated by PCR using primers allowing directional cloning between the XhoI and KpnI sites of pRS316 to yield pRS316.CYCt. The primers used were as follows:
5'-agacctcgagcatgcatctagaGGGCCGCATCATGTAATTAG-3' (SEQ ID NO. 5) and 5'agacggtaccGGCCGCAAATTAAAGCCTTC-3' (SEQ ID NO. 6). The T7 promoter and SV5 epitope-tag coding sequence was synthesised as an oligonucleotide containing 5'-BamHI and 3'XhoI restriction sites. This was then cloned into the pRS316.CYCt between the BamHI and XhoI sites. Finally, the BamHI-KpnI fragment from pRS316 containing the entire T7 promoter, SV5 epitope coding sequence and the CYC terminator was inserted between the Bg/II site downstream from the sequence encoding the VP16 activation domain and the KpnI site in pRS316 to give pWITCH.URA. To make a version of pWITCH containing the TRP1 gene, the entire cassette isolated as a KpnI-NaeI fragment was transferred to a modified version of pRS314 which has the BstXI site within the TRP1 gene mutated. The mutation of the BstXI site was achieved by PCR mutagenesis and resulted in the sequence of the natural BstXI site being changed from CCAACTGCATGGA (SEQ ID NO. 7) to aCAACTGCATGGA (SEQ ID NO. 8).

Example 2
Functional testing of pWITCH ex vivo

To determine whether the various features of the pWITCH vector were functional, a cDNA encoding a deletion mutant of the yeast Pho4 transcription factor, extending between amino acids 156 and its C-terminus at amino acid 312, was inserted into the unique BamHI cloning site, in frame with both the VP16 activation domain and the SV5 epitope tag. This Pho4 mutant, which contains a fully functional DNA-binding and dimerisation domain but lacks sequences required for transcription activation (Jayaraman et al., 1994), is able to recognise two E-box motifs present in the PHO5 UAS. Transformation of yeast (S.cerevisiae) with a PHO5 UAS-CYC-LacZ reporter (Fisher et al., 1991) together with pWITCH expressing the VP16-Pho4▲N156 chimera resulted in efficient transcription activation when galactose was used as a carbon source (FIG. 2A, lane 1) and was dependent on the presence of an intact PHO5 UAS (data not shown). No significant activation was seen if yeast cells were grown in glucose (lane 2). The VP16 activation domain is therefore fully functional when fused to proteins expressed from pWITCH.

Figure 2:
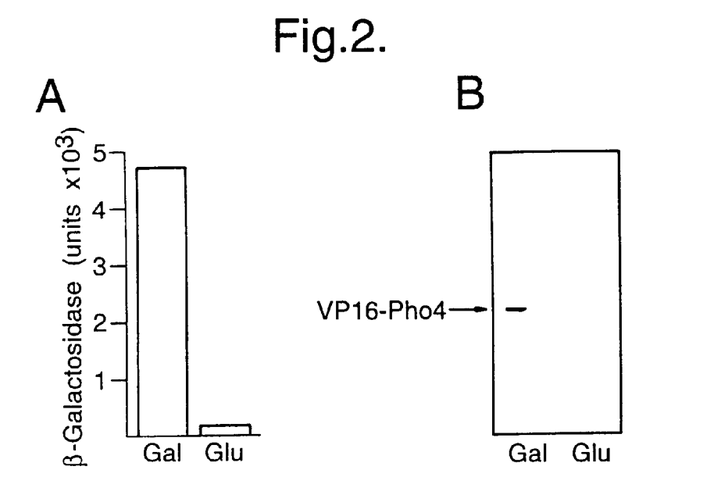
FIGS. 2A, 2B, 3A and 3B show results of functional testing of the construct of FIG. 1, described in Examples 2 and 3.

Next yeast cells producing the VP16-Pho4▲N156 were lysed, and the extract obtained was subjected to analysis by SDS-PAGE followed by western blotting. The western blot was then probed with the anti-SV5 monoclonal antibody. As expected, a single band of molecular weight corresponding to the VP16-Pho4▲N156 chimeric protein was observed when expression was induced using galactose as a carbon source but not when glucose was used (FIG. 2B). No band was observed using extract from expressing yeast together with a control, anti-v-Jun antibody (not shown). Thus, as expected, proteins produced ex vivo from pWITCH possess both a functional VP16 activation domain and are tagged with the SV5 epitope. Moreover, the SV5 epitope appears highly specific, with no evidence for recognition of endogenous yeast proteins by the anti-epitope antibody.

The procedure for expression from pWITCH in vivo was as follows:

A. The pWITCH vector containing a cDNA encoding the ▲N156 Pho4 mutant protein was transformed into yeast together with a reporter (Fisher et al., 1991) containing the PHO5 UAS upstream of the lacZ gene. After growth in glucose or galactose minimal medium transformants were assayed for β-galactosidase activity. Yeast were transformed following the procedure of Hinnen (Hinnen et al., 1978). For liquid β-galactosidase assays, yeast colonies were picked into 6 ml glucose minimal medium supplemented with the appropriate amino acids and grown for 24–48 h. The cells were then pelleted by low speed centrifugation, resuspended in 1 ml minimal medium and 100 µl transferred into 6 ml fresh galactose or glucose minimal medium as indicated. After 18 h at 30° C. the cells were harvested by centrifugation, washed in H$_2$O and resuspended in 100 µl buffer containing 0.1M Tris.HCl pH 7.5, 0.05% Triton X-100 before freezing. Assays for B-galactosidase activity were then performed as described previously (Harshman et al., 1988).

B. Western blot using anti-SV5 antibody as a probe to detect the epitope-tagged VP16-▲N156 Pho4 chimera produced in yeast after growth in glucose or galactose minimal medium as indicated. Essentially 50 ml yeast culture grown to an O.D$_{600}$ 0.6 were harvested and washed with 15 ml PBS. All subsequent steps were performed at 4° C. The yeast cells were resuspended in 350 µl HSB buffer (45 mM Hepes KOH pH7.5, 400 mM NaCl, 10% glycerol, 1 mM EDTA, 0.5% NP40, 2 mM DTT, 2 mM Benzamide, 1 mM PMSF, leupeptin (1 mg/ml), pepstatin (1 mg/ml), 10 mM NaF, 10 mM calyculin A) and 300 µl equivalent acid washed glass beads added. The cells were lysed on a vibramax for 5 min and spun in a microfuge for 5 min. The supernatant was transferred to a new tube and centrifuged for a further 15 min. This supernatant was used as the lysate, 15 µl of which was mixed with an equal volume of 'boiling blue' (50 mM Tris.HCl pH 6.8, 600 mM β-mercaptoethanol, 2% SDS, 0.1% bromophenol blue, 10% glycerol), the samples boiled for 2 min and 15 µl loaded to a mini 15% SDS-PAGE gel. After transfer to nitrocellulose, the blot was probed sequentially with anti-SV5 antibody in 10% calf serum/PBS. Alkaline phosphatase coupled to anti-mouse immunoglobulin G was used as the second antibody and the bands visualised using BCIP/NBT as substrate.

Example 3
Functional testing of pWITCH in vitro

Figure 3:
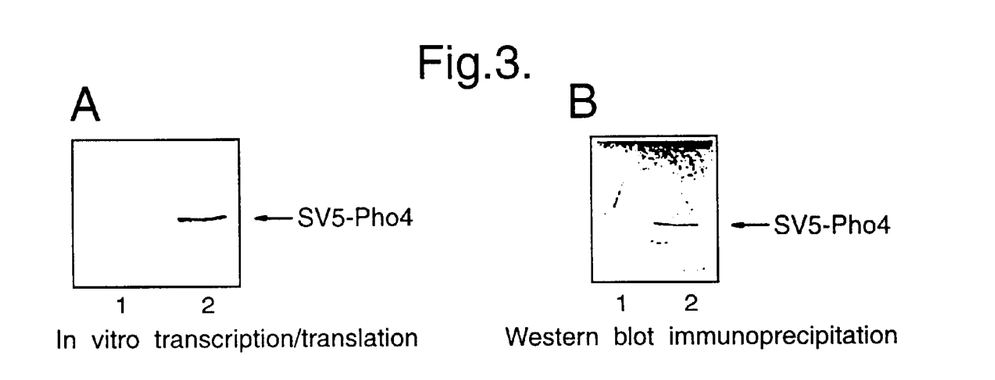

A feature of a pWITCH is the inclusion of the T7 promoter to enable expression of SV5-tagged proteins by in vitro transcription/translation. To test whether this aspect of pWITCH was fully functional, the pWITCH derivative encoding the ▲N156 Pho4 mutant in a T7-coupled TNT (Promega) was used in an in vitro transcription/translation reaction. Using $^{35}$S-methionine, a labelled product of the appropriate size was readily detected after analysis by SDS-PAGE and autoradiography (FIG. 3A, lane 2). No product was observed using an unprogrammed lysate (lane 1). An unlabelled translation product was also prepared in parallel and analysed first by immunoprecipitation using the anti-SV5 antibody followed by SDS-PAGE and western blotting. Again, a band of the appropriate size was detected if the translation product was immunoprecipitated using the anti-SV5 antibody (FIG. 3B, lane 2), but not if a heterologous antibody (anti-v-Jun) was used (lane 1). Thus, pWITCH can be used to produce SV5-tagged and immunoprecipitatable protein from an in vitro transcription translation reaction.

The procedure for expression from pWITCH in vitro was as follows:

A. A standard in vitro transcription/translation reaction (TNT kit, Promega) was programmed using either 1 μg of an empty pBluescript vector (lane 1) or 1 μg of pWITCH containing the PHO4▲N156 cDNA (lane 2) and $^{35}$S-methionine-labelled protein visualised after SDS PAGE and autoradiography.

B. Western blot using anti-SV5 epitope antibody of immunoprecipitated unlabelled SV5-▲N156 Pho4 chimeric protein produced by in vitro transcription/translation using the pWITCH vector. The translated protein was immunoprecipitated by rolling with 10 μl protein A sepharose beads (precleared for 1 h with normal rabbit serum) together with either anti-c-Jun antibody (lane 1) or anti-SV5 epitope antibody (lane 2) in the presence of 0.5 μl normal rabbit serum. After incubation for 4 h the beads were then washed 4 times with 200 μl PBS. Finally 25 μl SDS-PAGE loading buffer was added and the samples processed for SDS-PAGE and western blotting using the anti-SV5 epitope antibody as described in Example 2.

Example 4

The design of the two-hybrid vectors pDM22 and pDM26

The relevant parts of the two-hybrid vectors pDM22 and pDM26, are shown in FIG. 5A and FIG. 5B respectively.

The plasmid pDM22 is an activator plasmid encoding the GAL4 transcriptional activation domain expressed from a yeast ADH1 promoter. Downstream of the transcriptional activation domain is a translationally in frame T7 promoter which is functional in vitro and in certain strains of E.coli (for example BL21 (Novagen)). Downstream of the T7 promoter are two tags, a (histidine)$_6$ tag, for purification of proteins (Hochuli et al, 1988) and a T7 epitope tag (Lutz-Freyermuth et al, 1990). Following the tags is a polylinker for cloning of the gene of interest and translation stop codons, followed finally by the ADH1 terminator. In this example a truncated S. cerevisiae PHO4 gene has been cloned in frame into the polylinker to form pNW05. Transformation of pNW05 into yeast will result in the expression of a GAL4 transcriptional activation domain tagged PHO4▲N156, which will be functional as an activator plasmid in a two-hybrid assay. In vitro transcription and translation from the T7 promoter or transformation into T7 polymerase containing strains of E.coli will result in the expression of a T7 epitope, (His)$_6$ tagged PHO4▲N156.

The bait plasmid pDM26 contains the ADH1 promoter followed by a LexA DNA binding domain, a translationally in frame T7 promoter, a S tag, a polylinker, translation stop codons and finally an ADH1 terminator. In this example a PHO80 gene has been cloned in frame into the polylinker to produce pDM27. Transformation into yeast will result in the expression of a LexA DNA binding domain tagged PHO80, which will be functional as a bait plasmid in a two-hybrid assay. In vitro transcription and translation from the T7 promoter or expression within T7 polymerase containing strains of E.coli will produce an S tagged PHO80 protein.

In order to carry out a two-hybrid assay, plasmids encoding the two-hybrid proteins (activator and bait) are co-transformed into yeast. This will result in the expression of a GAL4 activation domain-PHO4 protein and a LexA DNA binding domain-PHO80 hybrid protein. Interaction of these two-hybrid proteins will reconstitute a transcriptional activator which can turn on the expression of a reporter gene expressed from a promoter under the control of a lexA operator.

The activator plasmid pDM22 was constructed as follows: oligonucleotides with the following sequence were synthesized and annealed (Oswell, University of Edinburgh, Edinburgh, UK). The oligonucleotides had the following sequences: 5'-CAG ATC TAT TAA TAC GAC TCA CTA TAG GGA GAC CAC AAG GTT TCC ATC TAG AGT TCT TTA CAA GAG AAG GAG TTC CCT GCA GGC AGC TGT GTG GAT CCA TGG TAC CAG CGG CCG CTA GCT AGC TGA CTC GAG G-3' (SEQ ID NO. 9) and 5'-CCT CGA GTC AGC TAG CTA GCG GCC GCT GGT ACC ATG GAT CCA CAG CTG CCT GCA GGG AAC TCC TTC TCT TGT AAA GAA CTC TAG ATG GAA ACC TTG TGG TCT CCC TAT AGT GAG TCG TAT TAA TAG ATC TGA GCT-3' (SEQ ID NO. 10). The oligonucleotide cassette was inserted between the SstI and SphI sites of pUC118 to produce pDM5. A second pair of oligonucleotides were synthesized and hybridised. The sequence of these oligonucleotides was: 5'-GGG TAT GCA CCA CCA CCA CCA CCA CGC TAT GGC TAG CAT GAC TGG CGG TCA GCA AAT GGG TAG AAT TCA AAC CAG TGT GCT GGA GTT AAC AAA GCT TAA GTC GAC CAT CAC ACT G-3' (SEQ ID NO. 11) and 5'-GAT CCA GTG TGA TGG TCG ACT TAA GCT TTG TTA ACT CCA GCA CAC TGG TTT GAA TTC TAC CCA TTT GCT GAC CGC CAG TCA TGC TAG CCA TAG CGT GGT GGT GGT GGT GGT GCA TAC CCT GCA-3' (SEQ ID NO. 12). The oligonucleotide cassette was then inserted into the PstI and BglII sites of DM5, creating pDM8. Meanwhile the oligonucleotides 5'-AAT TGA GAT CTG ATA TCG GTC CCT CGA G-3' (SEQ ID NO. 13) and 5'-GAT CCT CGA GGG ACC GAT ATC AGA TCT C-3' (SEQ ID NO. 14) were hybridised and inserted into the EcoRI and BglII sites of pGAD424 (Bartel et al, 1993) to form pDM20. The long oligonucleotide was excised from pDM8 using the restriction enzymes BglII-XhoI and cloned into the BglII-XhoI sites of pDM20 to create pDM21. An error in the cloned oligonucleotide sequence was corrected using the following oligonucleotides: 5'-GGA TTT CGA AAT GCA CCA CCA CCA CCA CCA CGC TAT GG-3' (SEQ ID NO. 15) and 5'-CTA GCC ATA GCG TGG TGG TGG TGG TGG TGC ATT TCG AAA TCC TGC A-3' (SEQ ID NO. 16) which were hybridized and cloned into the PstI-NheI sites of pDM21 to create the plasmid pDM22.

The bait plasmid was constructed as follows: the LexA DNA binding domain was amplified by PCR using the primers 5'-GGA AGC TTA TGA AAG CGT TAA CGG CCA GGC AAC AAG AGG-3' (SEQ ID NO. 17) and 5'-GAA GCT TCT CGA GGA GAT AGA TCT CAG CCA GTC GCC GTT GCG-3' (SEQ ID NO. 18). The PCR product produced was cut with HindIII and cloned into pGAD424. The resulting plasmid pDM24 therefore contains the LexA DNA binding domain expressed from the ADH1 promoter. Meanwhile the following oligonucleotides were synthesised encoding the S tag: 5'-GGG TAT GAA AGA AAC CGC TGC TGC TAA ATT CGA AAG ACA GCA CAT GGA CAG CGA TAT CAG-3' (SEQ ID NO. 19) and 5'-AAT TCT GAT ATC GCT GTC CAT GTG CTG TCT TTC GAA TTT AGC AGC AGC GGT TTC TTT CAT ACC CTG CA-3' (SEQ ID NO. 20). After hybridisation, this oligonucleotide was inserted between the PstI and EcoRI sites of a plasmid containing the BglII-XhoI oligonucleotide. The oligonucleotide was excised using BglII and XhoI and then cloned into the BglII-XhoI sites of pDM24 to create pDM25. Finally the SphI fragment from pDM25 was cloned into the plasmid pDM23 (pGAD424 containing URA3 as a selectable marker, replacing LEU2). The plasmid created was called pDM26 and is the final bait plasmid.

The reporter construct used for the two-hybrid system was a plasmid containing a lacZ gene expressed from a CYC1 basal promoter under the control a 3 lexA operators. The plasmid was obtained by cutting the approximately 4 kb ScaI fragment from pGV256 (Jayaraman et al, 1994) and inserting it into the NaeI and PvuII sites of pRS413 (Sikorski and Hieter, 1989). This plasmid was called pDM28.

A truncated PH04 DNA fragment, PHO4▲N156 (Jayaraman et al, 1994) was obtained by PCR from pKV701 (PH04/VP16) using the primers: 5'-CGG ATC CGC AGA ATT CTT AAC AAG CGC AGA GGT AAA CC-3' (SEQ ID NO. 21) and 5'-GGG TCG ACC TCA CGT GCT CTC GTT C-3' (SEQ ID NO. 22). This fragment was cloned into pDM22 using the restriction enzymes EcoRI and SalI to create the plasmid pNW05. The PHO80 DNA sequence was obtained as a PCR product from the plasmid pV44ER.PHO80 (Jayaraman et al, 1994), using the primers: 5'-GCG CAG AAT TCG GAT CCA AAT GGA AAG CAC ATC AGG AGA A-3' (SEQ ID NO. 23) and 5'-AGA TCT AAT CTG CCT TTG ATC GCT TGT TA-3' (SEQ ID NO. 24). The EcoRI-BglII PHO80 fragment was inserted into the EcoRI and BamHI sites of pDM26 to obtain pDM27.

Figure 6:
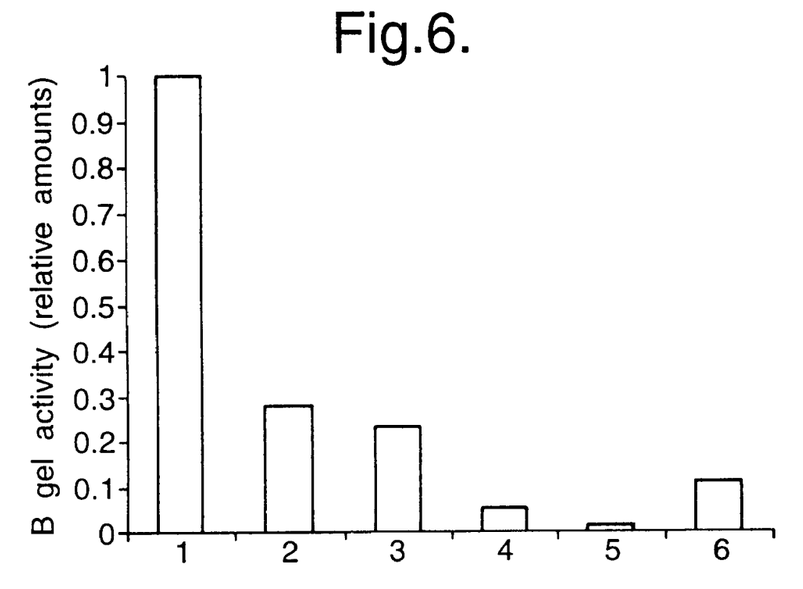
FIG. 6 shows the results from a two-hybrid assay in *S. cerevisiae* using the two-hybrid differential expression vectors based on pDM22 and pDM26.

Example 5
Functional testing of the plasmids pDM22 and pDM26 in a two-hybrid system ex vivo in S.cerevisiae The truncated PHO4 and PHO80 have been shown to interact previously in vivo in a yeast two-hybrid system (Jayaraman et al, 1994). In order to show that the differential expression vectors were functional in a two-hybrid assay, the truncated PHO4 and PHO80 sequences were cloned into the plasmids pDM22 and pDM26 to create pNW05 (the activator plasmid) and pDM27 (the bait plasmid) respectively. The two plasmids were transformed into S. cerevisiae strain YM4136 (MATα ura3-52 his3-200 ade2-101 lys2-801 trp1-901 leu2-3, 112 gal80-538) along with the LexA-CYC-LacZ reporter plasmid pDM28, by a lithium acetate method (Gietz et al, 1992). The β-galactosidase activity of individual yeast colonies was assayed as follows: an overnight culture was diluted in YPD media and grown at 30° C. until the yeast was in logarithmic phase. 1.5 ml of culture was pelleted, washed and the cells resuspended in 0.3 ml of Z buffer (60 mM $Na_2HPO_4$, 40 mM $NaH_2PO_4$, 10 mM KCl, 1 mM $MgSO_4$). The cells were lysed by freezing at −70° C. 0.7 ml of Z buffer was then added followed by 0.16 ml of 4 mg/ml ONPG in Z buffer. The tubes were incubated at 30° C. until a yellow colour developed. The reaction was stopped on the addition of 0.4 ml $Na_2CO_3$ and the absorbance read at 420 nm. There was an increased expression of LacZ in the case of yeast containing the three plasmids: pNW05, pDM27 and the reporter plasmid (FIG. 6, column 1) compared with yeast containing an pDM22 (the empty activator), pDM27 and reporter (column 2); pNW05, pDM26 (the empty bait) and reporter (column 3); pDM22, pDM26 and reporter (column 4); pNW05 and pDM27 (column 5) or reporter alone (column 6).

Figure 7:
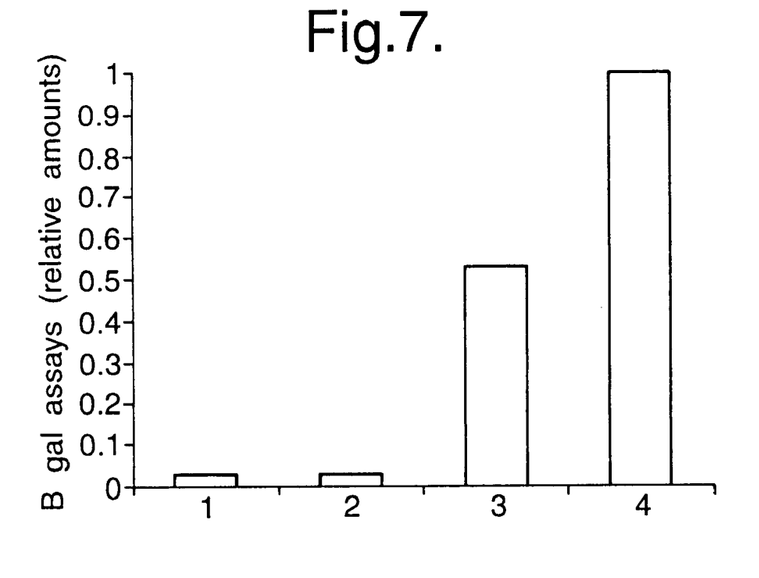
FIG. 7 shows data from a two-hybrid assay in *S.cerevisiae* which compares use of vectors which contain the T7 promoter for differential expression versus vectors which do not.

In order to establish if the presence of the T7 promoter was having an effect on the two-hybrid activity of the pNW05 activator plasmid, the truncated PHO4 was also cloned into pGAD424 to create pNW04. The PHO80 was cloned into the bait plasmid pGBT9 (Bartel et al, 1993) to form pNW06. A two-hybrid assay was carried out in the yeast strain Hf7c (MATα ura3-52 his3-200 ade2-101 trp1-901 leu2-3,112 gal4-542 gal80-538 LYS2::GAL1-HIS3 URA3::(GAL-17mers)$_3$). The β-galactosidase activity in the pNW05, pNW06 co-transformant (FIG. 7, column 4) was found to be higher compared with the β-galactosidase activity in a transformant containing pNW04, pNW06 (FIG. 7, column 3). No significant β-galactosidase activity was observed in yeast containing only pNW04 (FIG. 7, column 1) or pNW05 (FIG. 7, column 2). This experiment suggests that the presence of the in frame T7 promoter and epitope tags did not adversely affect the function of the activator plasmid in a two-hybrid assay. In fact the presence of the translated T7 promoter and the epitope tagged increased the β-galactosidase activity in the yeast. This could be because the presence of extra protein sequence that separates the GAL4 activation domain from the PHO4 domain, may reduce steric effects thereby allowing enhanced PHO4, PHO80 binding or enhanced GAL4 activated transcription of lacZ.

The above example has shown that differential expression vectors are functional when used in a two-hybrid system. There is no adverse change in the ability of an activator plasmid which contains an in frame T7 promoter to function in a two-hybrid assay compared to an activator plasmid without such a promoter.

Example 6
Functional testing of pDM22 and pDM26 in vitro

Figure 8A:
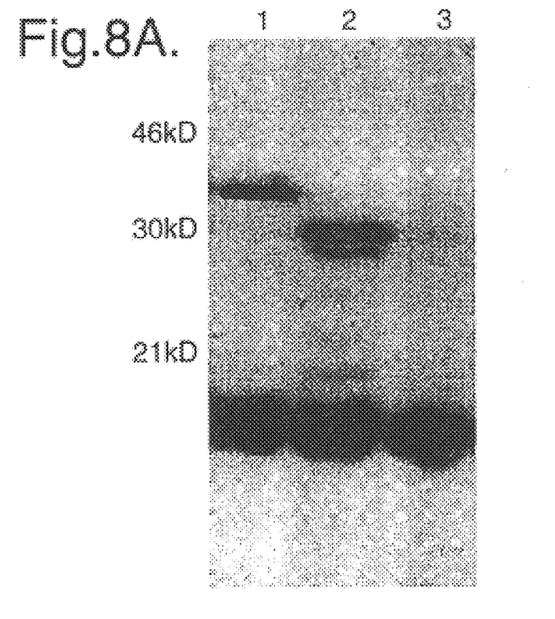
FIG. 8a shows a Western blot of biotinylated protein expressed differentially in vitro.

Both the plasmids were tested in vitro by carrying out an in vitro transcription reaction using 0.5 μg of plasmid pNW05 and pDM27 followed by an in vitro translation reaction using a rabbit reticulocyte lysate supplemented with biotinylated lysine-tRNA (Amersham). Protein produced was analysed by SDS-PAGE and Western blotting. The blot was probed with horse radish peroxidase labelled streptavidin (Amersham) and detected with ECL reagents (Amersham). A protein of the size 29 kD was observed (FIG. 8a, lane 2). An in vitro transcription, translation reaction programmed in the absence of plasmid did not produce the 29 kD protein (FIG. 8a, lane 3).

Figure 8B:
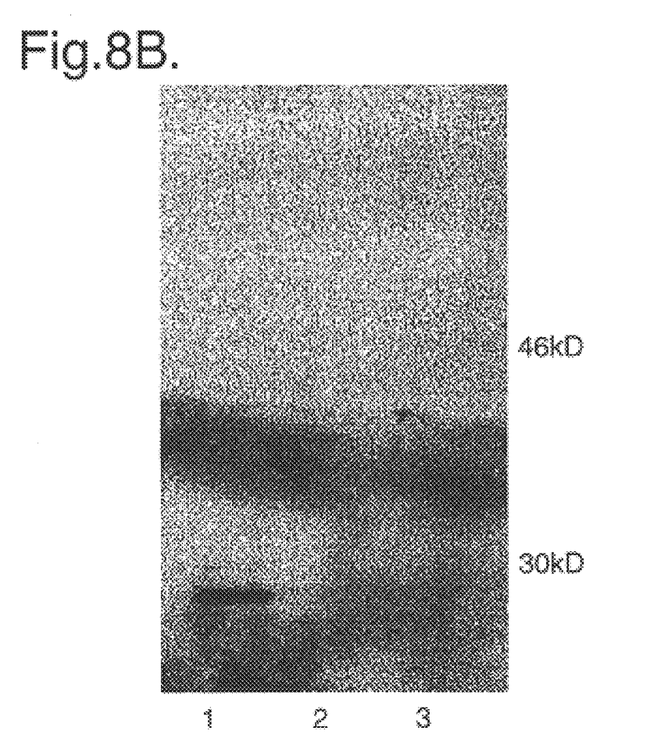
FIG. 8b shows a Western blot probed the products from in vitro transcription and translation with an antibody to the T7 epitope.

Additional evidence to indicate that the 29 kD protein was indeed the T7 epitope, $(His)_6$ tagged PHO4 produced from the in frame T7 promoter was the analysis of in vitro transcribed and translated reactions by Western blot. In vitro transcribed and translated protein was separated by SDS-PAGE and Western blotted. The blot was probed with a T7 epitope antibody (Novagen) followed by HRP labelled mouse antibody and detected with ECL reagents (Amersham). In the case of an in vitro transcription and translation reaction programmed with pNW05, a 29 kD protein was detected (FIG. 8b, lane 1). The 29 kD protein was not detected in an in vitro transcription and translation reaction programmed with pDM27 (FIG. 8b, lane 2) or in the absence of plasmid (FIG. 8b, lane 3).

Figure 8C:
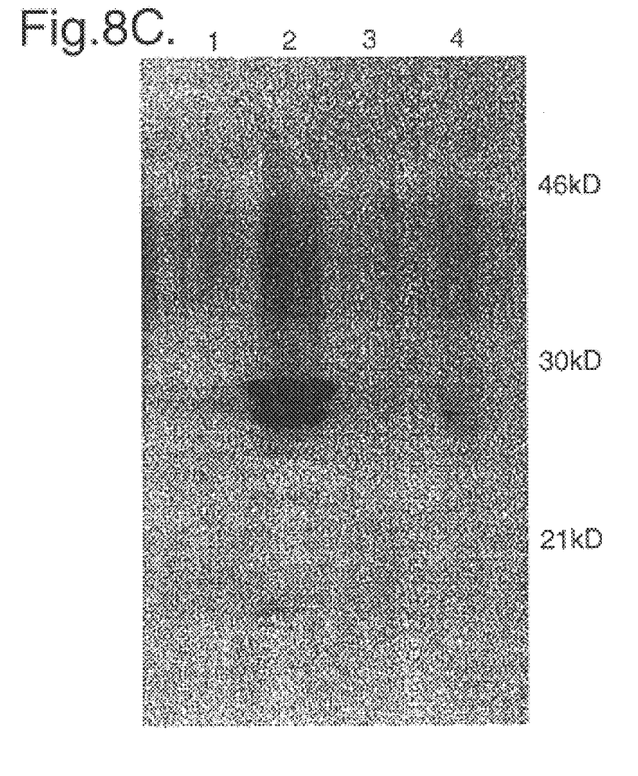
FIG. 8c shows a Western blot of the biotinylated products from in vitro transcription and translation probed with an HRP/streptavidin conjugate.

In addition, a transcription and translation reaction used conditions and detection as in FIG. 8a above. The template was the plasmid pNW04 (which contains the ADH1 promoter, GAL4 transcriptional activation domain and PHO4▲N156 but no in frame 17 promoter) and failed to show the 29 kD protein (FIG. 8c, lane 3). A similar reaction with pNW05 did show the 29 kD protein (FIG. 8c, lane 2). Lanes 1 and 4 are in vitro transcription, translation reactions programmed with pDM22 and in the absence of plasmid respectively. The size of the PHO4▲N156 may be larger than in Example 3 because the protein was tagged with the T7 epitope tag and $(His)_6$ tags. Furthermore a PCR mutation in the PHO4 had resulted in a duplication of the primer at the 3' end of the cloned gene. The plasmid pDM27 produced an approximately 36 kD size protein in a transcription, translation reaction. This was the predicted size of the S tagged PHO80 (FIG. 8a, lane 1).

Example 7
Functional testing of pDM22 and pDM26 ex vivo in *E.coli*

Some strains, for example BL21, contain T7 RNA polymerase integrated in the chromosome (Novagen). The expression of T7 RNA polymerase is induced by IPTG. The in frame T7 promoter should therefore be functional in such strains and produce, in the case of the pNW05 transformant, a T7 and (His)$_6$ tagged PHO4.

Figure 9:
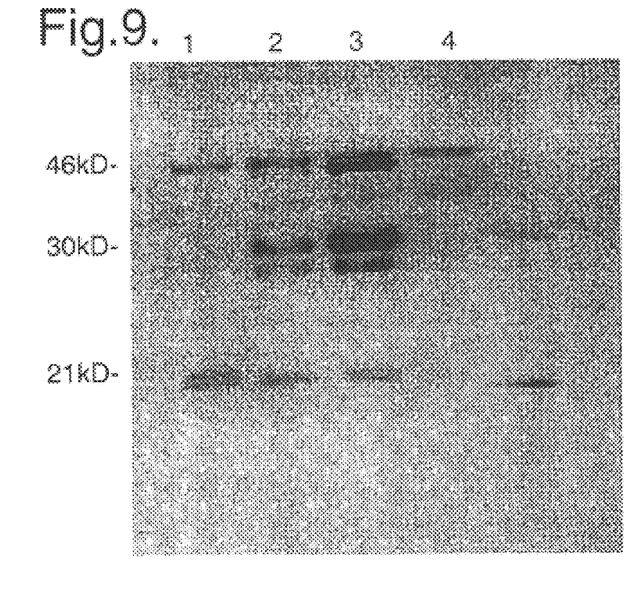
FIG. 9 shows a Western blot of *E. coli* lysates probed with a T7 epitope antibody.

In order to test the protein expression from a differential expression vector in *E.coli*, the plasmid pNW05 was transformed into the *E.coli* strain BL21 (Novagen) and plated on L-agar containing 50 μg/ml carbenicillin. The cells were grown in liquid culture (L-broth containing 50 μg/ml carbenicillin) until they were in logarithmic phase. IPTG was added to 0.4 mM and the cells were grown for a further 2 hours. Cells were harvested by centrifigation and lysed by boiling in SDS-PAGE loading buffer (0.2 M Tris pH 6.8, 1% SDS, 0.1% bromophenol blue, 40% glycerol) for 5 mins. Cellular debris was removed by 10 minutes centrifugation in a microfuge. Protein extracts from *E.coli* were analysed by SDS-PAGE followed by Western blotting (FIG. 9). The membrane was probed with a 1/10,000 dilution of T7 epitope antibody (Novagen) followed by a 1/10,000 dilution of HRP labelled anti-mouse (Amersham) and detected using ECL reagents (Amersham). The following extracts were loaded: lane 1, untransformed *E.coli*, uninduced; lane 2, pNW05 transformant, uninduced; lane 3, pNW05 transformant, induced with 0.4 mM IPTG; lane 4 untransformed *E.coli*, induced with 0.4 mM IPTG. A protein of 29 kD was detected with the T7 epitope antibody within the induced pNW05 transformant. This is the size predicted by the in vitro transcription and translation experiment described in Example 6 and is likely to represent the T7 epitope and (His)$_6$ tagged PHO4.

Differential expression vectors in the two-hybrid assay, can be used as both the activator plasmid and also the bait plasmid. It is therefore possible to produce both the bait and activator proteins rapidly in vitro or in *E.coli* and test for their interaction in an alternative in vitro protein protein interaction assay, such as co-immunoprecipitation. The ability to confirm that a novel interaction detected in the yeast 2-hybrid assay also occurs in vitro would support the idea that a genuine interaction has been detected rather than a false positive. In addition, the possible influence of post-translational modifications can be examined. For example, if an interaction occurs in vivo but not in vitro one possible explanation may be that the protein was being post-translationally modified in vivo.

The use of in vitro transcription and translation may also be useful in order to ensure that the gene of interest has been inserted correctly into the bait vector before commencing a two-hybrid screen.

Expression in *E.coli* enables large quantities of protein to be purified rapidly for generation of an antibody or to set up a high through put screen based on a protein interactions in vitro such as in drug assay formats.

REFERENCES

Berger,S. L., Pina,B., Silverman,N., Marcus,G. A., Agapite, J., Regier,J. L., Triezenberg,S. J. and Guarente,L. Cell 70 (1992) 251–265.

Cousens,D. J., Greaves,R.,Goding,C. R. and O'Hare,P. EMBO j.8 (1989) 2337–42.

Fields,S. and Song,O. Nature 340 (1989)245–246.

Fisher,F., Jayaraman,P. S. and Goding,C. R.

Oncogene 6 (1991) 1099–1104.

Hanke,T., Szawlowski,P and Randall,R. E. J.Gen.Virol.73 (1992) 653–660.

Harshman, K. D. et al. Cell 53 (1988) 321–330.

Hinnen,A., Hicks,J. B., and Fink,G. R. Proc.Natl. Acad.Sci. USA 75 (1978) 1929–33.

Hirst,K., Fisher,F., McAndrew,P. C. and Goding,C. R. EMBO J.B. (1994) 5410–5420.

Jayaraman, P. S., Hirst, K. and Goding, C. R. EMBO J.13 (1994) 2192–9

Sikorski,R. S. and Hieter,P. Genetics 122 (1989) 19–27.

Hochuli, E., Bannwarth, W., Dobeii, H., Gentz, R. and Stuber, D. (1988)

Biotechnology 6 1321–1325

Lutz-Freyermuth, C., Query, C. C. and Keene, J. D. (1990) Proc Natl Acad Sc USA 87 6393–6397

Gietz D., St Jean, A., Woods, R. A. and Schiestl, R. H. (1992) Nucl Acid Res Bartel P. L., Chien, C.-T., Sternglanz, R. and Fields, S. (1993) In Cellular Interactions in development: A Practical Approach (Oxford University Press, Oxford), p 153–179.

---

We claim:

1. A DNA construct for investigating a protein, which DNA construct comprises:
   (a) a first promoter
   (b) a chimeric gene comprising a DNA sequence that encodes a fusion protein, said DNA sequence under transcriptional control of the first promoter, such that in a suitable host cell the fusion protein is expressed, the fusion protein comprising:
      (i) a first domain for detecting, quantifying or giving a specific function to the fusion protein;
      (ii) a second domain which is the protein of interest; characterised in that within the chimeric gene is a second promoter capable of initiating transcription of a portion of the chimeric gene encoding one of the two domains of the fusion protein without the other domain, and the two promoters operate under different conditions.

2. A DNA construct as claimed in claim 1, wherein the second promoter initiates transcription of a portion of the chimeric gene encoding the second domain of the fusion protein without the first domain.

3. A DNA construct at claimed in claim 1, wherein the second promoter initiates transcription in vitro.

4. A DNA construct as claimed in claim 3, wherein the second promoter is a bacteriophage promoter.

5. A DNA construct as claimed in claim 1, wherein the first promoter is a yeast or a mammalian promoter.

6. A DNA construct as claimed in claim 1, wherein the first domain is either the DNA-binding domain or the transcriptional activation domain and the second domain is a test protein which is to be tested for interaction with another test protein.

7. A DNA construct as claimed in claim 6, suitable for use in a two-hybrid assay.

8. A DNA construct as claimed in claim 1, further comprising within the chimeric gene and in the same reading frame as the first and second domains a DNA sequence encoding an epitope tag.

9. A DNA construct as claimed in claim 8, wherein the DNA sequence encoding the epitope is under transcriptional control of both the first and the second promoter.

10. A DNA construct as claimed in claim 1, wherein the portion of the chimeric gene encoding the second domain of the fusion protein is absent and the chimeric gene contains at least one cloning site for insertion of the absent portion.

11. A DNA construct as claimed in claim 1 in the form of an expression vector.

12. A host cell containing a DNA construct or a vector as claimed in claim 1.

13. A method for differential expression of a chimeric protein having at least two domains, comprising:

providing a vector containing a DNA sequence in which a first promoter controls transcription of all of the domains and a second promoter controls transcription of one or more but not all of the domains, the promoters being operational under different conditions;

subjecting the vector to a first set of conditions to effect transcription under the control of the first promoter and expression of a protein comprising all of the domains;

subjecting the vector to a second set of conditions to effect transcription under the control of the second promoter and expression of a protein comprising one or more but not all of the domains.

14. The DNA construct according to claim 11, wherein the expression vector is a plasmid.

* * * * *